(12) United States Patent
Lee et al.

(10) Patent No.: US 6,670,458 B2
(45) Date of Patent: Dec. 30, 2003

(54) PROCESS FOR PREPARATION OF L-RIBOSE USING 1,4-LACTONE

(75) Inventors: Sang Jo Lee, Taejeon (KR); Myung Joon Seo, Taejeon (KR); Nak Cheol Jeong, Taejeon (KR); Gun Cheol Kim, Taejeon (KR); Hyun Woung Hong, Taejeon (KR); Sul A Kim, Taejeon (KR)

(73) Assignee: Hanchem Co., Ltd., Taejeon (KR)

( * ) Notice: Subject to any disclaimer, the term of this patent is extended or adjusted under 35 U.S.C. 154(b) by 257 days.

(21) Appl. No.: 09/931,020

(22) Filed: Aug. 17, 2001

(65) Prior Publication Data

US 2002/0035250 A1 Mar. 21, 2002

(30) Foreign Application Priority Data

Aug. 19, 2000 (KR) ........................................ 2000-48068

(51) Int. Cl.$^7$ ................................................ C07H 15/00
(52) U.S. Cl. ........................ 536/4.1; 549/283; 549/306
(58) Field of Search .......................... 536/4.1; 549/283, 549/306

(56) References Cited

PUBLICATIONS

Munier et al., Tetrahedron Letters, vol. 34(51), pp. 8241–8244. (1993).*

* cited by examiner

*Primary Examiner*—James O. Wilson
*Assistant Examiner*—Howard V. Owens, Jr.
(74) *Attorney, Agent, or Firm*—Birch, Stewart, Kolasch & Birch, LLP

(57) ABSTRACT

The present invention relates to a process for effectively preparing L-ribose, which is recognized as being highly important in relation to the development of new antiviral medicines, from 1,4-lactone compound.

8 Claims, No Drawings

PROCESS FOR PREPARATION OF L-RIBOSE USING 1,4-LACTONE

TECHNICAL FIELD

The present invention relates to a process for effectively preparing L-ribose from a 1,4-lactone compound.

BACKGROUND ART

L-ribose is widely used as raw materials for food, cosmetics or medicines. Recently, as physiological functions of L-nucleosides have been gradually discovered with the support of genetic engineering, new medicines containing L-nucleoside as active ingredient are newly developed and thus, the demand for L-nucleosides are on the increase. Particularly, demand for L-ribose is highly increased as it is the key intermediate for BW1263w94(Glaxo Wellcome) as antiherpes and L-FMAU (Bukwang & Triangle) as antihepatitis B. Thus, many researchers in this field are interested in the development of an industrially applicable process for preparing the same (see: Nucleic acid & Nucleotide 18(2), 187(1999); JP 11/12294; WO 98/39347). In this regard, recently, there has been developed a process for preparing L-ribose and rare sugars using an enzyme controlling the chirality (see: WO 99/61648).

However, since the existing processes for the preparation of L-ribose had the problems of low production yield and productivity, a new effective process was strongly required. Complying with such a requirement, more effective chemical processes have been filed and patented. The researches were much more activated recently, and as a result thereof, even a biological method using an enzyme has come.

Hitherto, L-ribose of the following formula (1) was conventionally prepared from L-arabinose of the following formula (2). That is, the hydroxy group at $C_2$ position of L-arabinose was stereoselectively converted to give L-ribose.

(1)

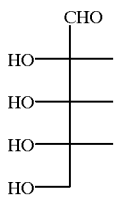

(2)

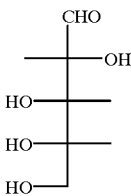

One of the methods for providing L-ribose from L-arabinose proceeds via L-arabinal intermediate as depicted in the following Scheme 1 (see: J. Am. Chem. Soc., 56, 1152 (1934)). However, this method has some problems in economy due to the low yield:

Scheme 1

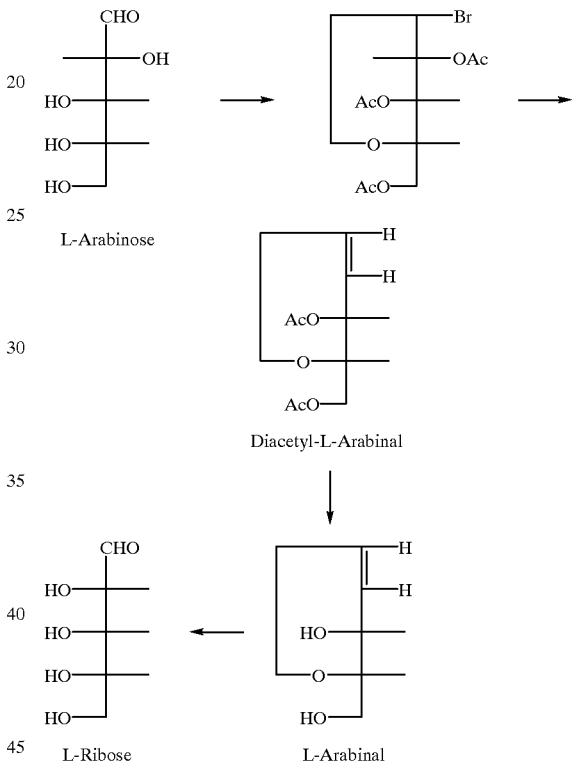

Further, as depicted in the following Scheme 2, the $C_2$ position of L-arabinose may be oxidized by pyridine dichromate and then reduced by sodium borohydride ($NaBH_4$) to provide L-ribose in a considerably high yield. However, since it is difficult to handle pyridine dichromate, said method can hardly be applied to an industrial production (see: Nucleosides & Nucleotides, 18(2), 187(1999)).

Scheme 2

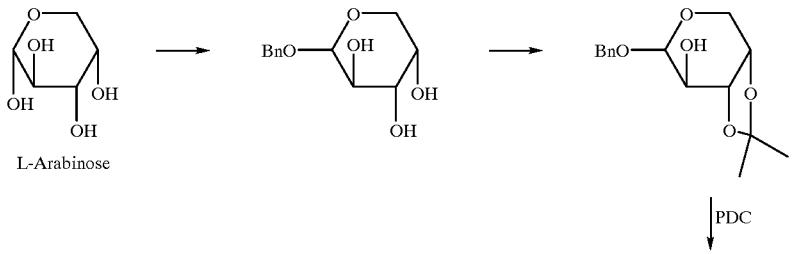

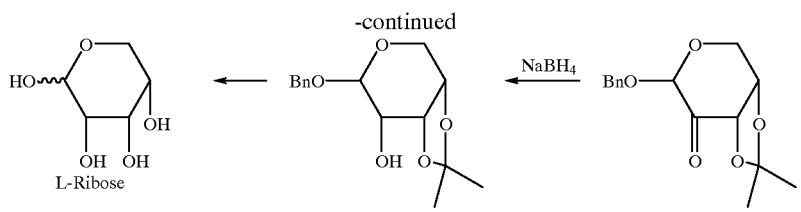

Recently, a method wherein $C_2$ position is stereoselectively converted in a direct manner using molybdenium trioxide ($MoO_3$) as a catalyst has been developed. However, the yield of this method is low, and it is not easy to isolate and purify the resulting L-ribose from the reactants (see: JP 11-12,294). Further, an American researcher has developed a new type of process for preparing L-ribose from D-ribose (Formula III), that is, a process wherein $C_1$ aldehyde group of D-ribose is reduced and $C_5$ hydroxy group is oxidized to give L-ribose (see: the following Scheme 3). But, the problems thereof such as extremely low reaction temperature of −78° C., the nasty smell of sulfides, etc. should be solved first for the process to be industrially applied (see: WO 98/39,347).

Scheme 3

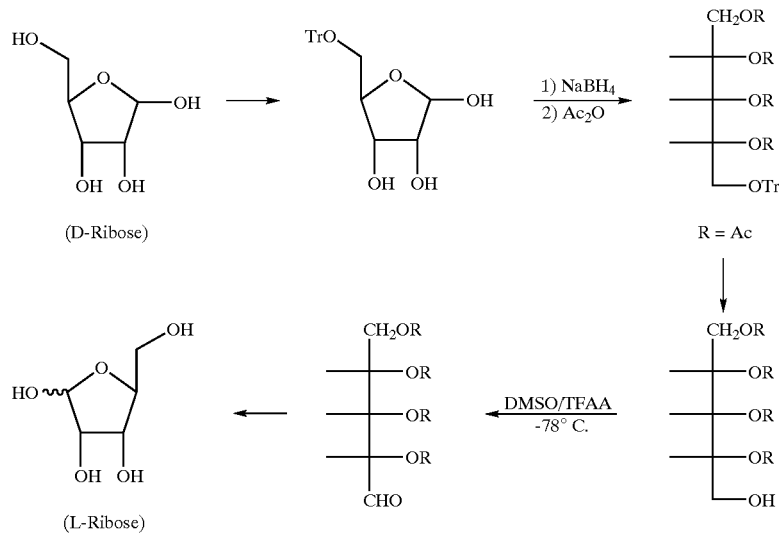

For the purpose of overcoming the problems encountered in the synthetic methods as explained above, a Japanese researcher has designed a process for preparing L-ribose using a specific enzyme (L-ribose isomerase). This process proceeds considerably smoothly due to the use of an enzyme. However, it also has the problems to be solved for its industrial application. That is, economical and stable supply of the starting material ribitol has to be secured (see: WO 99/61,648).

DISCLOSURE OF INVENTION

Thus, the present inventors, who were keenly aware of the problems, have extensively studied to develop an economical and convenient process for obtaining L-ribose under the recognition of the absolute need thereof. As a result, we have identified that such a purpose can be achieved by a process as explained below, and then completed the present invention.

Therefore, an object of the present invention is to provide a process for effectively preparing L-ribose.

BEST MODE FOR CARRYING OUT THE INVENTION

The present invention relates to a process for preparing L-ribose of formula (1) characterized in that (a) a compound of the following formula (3):

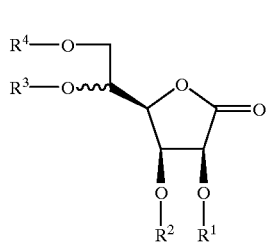

(3)

wherein $R^1$, $R^2$, $R^3$ and $R^4$ independently of one another represent $C_2$–$C_6$-carbonyl, benzoyl or benzyl, or $R^1$ and $R^2$, or $R^3$ and $R^4$ may combine with each other to form isopropylidene or cyclohexylidene, is reacted with a secondary amine of the following formula (4):

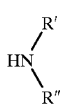

(4)

wherein R' and R" are identical with or different from each other and independently of one another represent straight-chain or branched $C_1$–$C_6$-alkyl, or may combine together with the nitrogen atom to which they are attached to form 4- to 7-membered saturated heterocycle, and then reacted with a sulfonyl group-containing compound of the following formula (5):

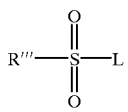

(5)

wherein R''' represents straight-chain or branched $C_1$–$C_6$-alkyl, phenyl or tolyl, and L represents reactive leaving group, preferably halogen or

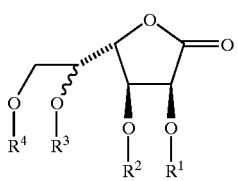

to give a compound of the following formula (6):

(6)

wherein $R^1$, $R^2$, $R^3$ and $R^4$ are defined as above, which has a converted chirality at 4-position carbon as compared with the compound of formula (3);

(b) the compound of formula (6) is reduced by DIBAL-H and then reacted with a compound of the following formula (7):

RX (7)

wherein R represents benzyl, benzoyl, $C_1$–$C_4$-alkanoyl or $C_1$–$C_4$-alkyl, and X represents halogen, to give a compound of the following formula (8):

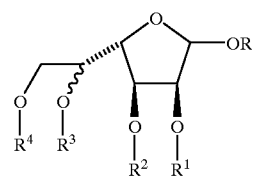

(8)

wherein $R^1$, $R^2$, $R^3$, $R^4$ and R are defined as above;

(c) the compounds of formulae (6) and (8) are reacted with periodic acid and then reduced by DIBAL-H or $NaBH_4$ to give compounds of the following formulae (9) and (10), respectively:

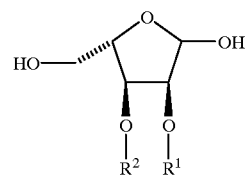

(9)

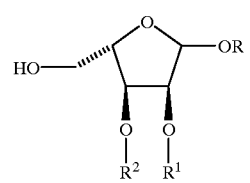

(10)

wherein $R^1$, $R^2$ and R are defined as above; and (d) the compound of formula (9) or (10) thus obtained is subjected to a hydrolysis reaction in a solvent.

The process for preparing L-ribose according to the present invention can be summarized as the following Scheme 4.

Scheme 4

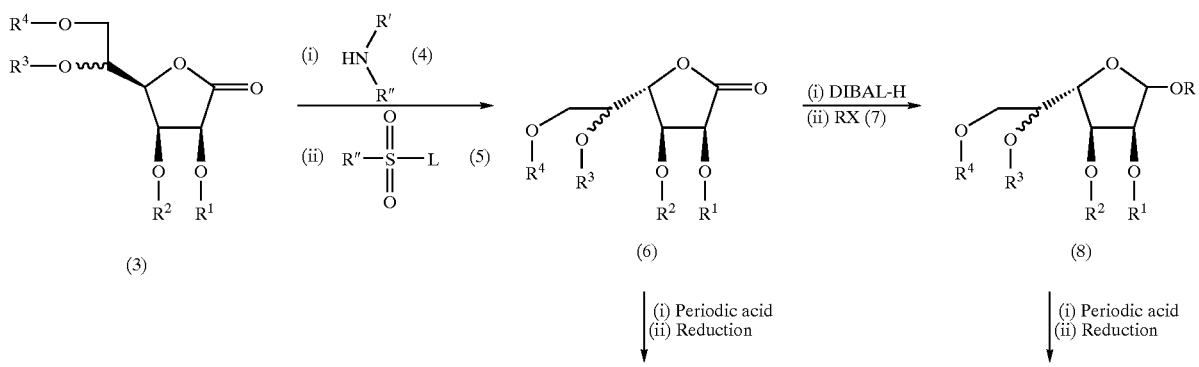

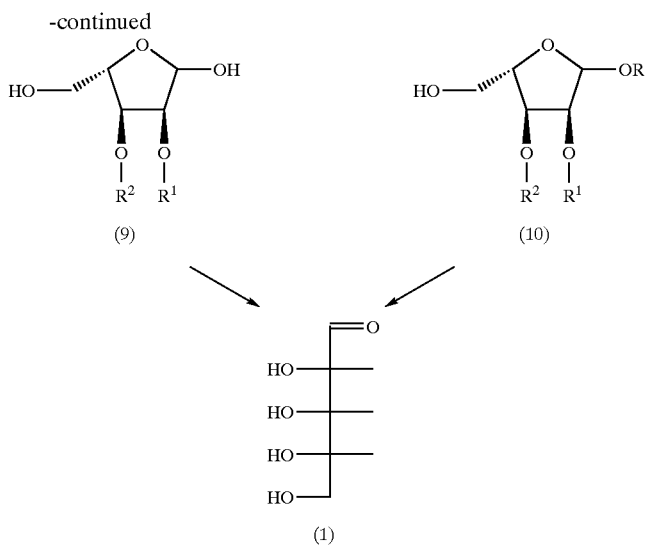

Hereafter, the process of the present invention will be more specifically explained step by step.

First, in Step (a), the 1,4-lactone compound of formula (3) is reacted with the secondary amine of formula (4) and then reacted with the sulfonyl group-containing compound of formula (5) to convert the chirality of 4-position carbon. As the similar chirality conversion process known in the art, there can be mentioned a process wherein a 1,5-lactone compound is reacted with benzyloxyamine (a primary amine) and then subjected to Mitsunobu reaction to convert the chirality of 5-position carbon in a comparatively high yield, as depicted in the following Scheme 5 (see: J. Am. Chem. Soc., 122, 2995(2000)):

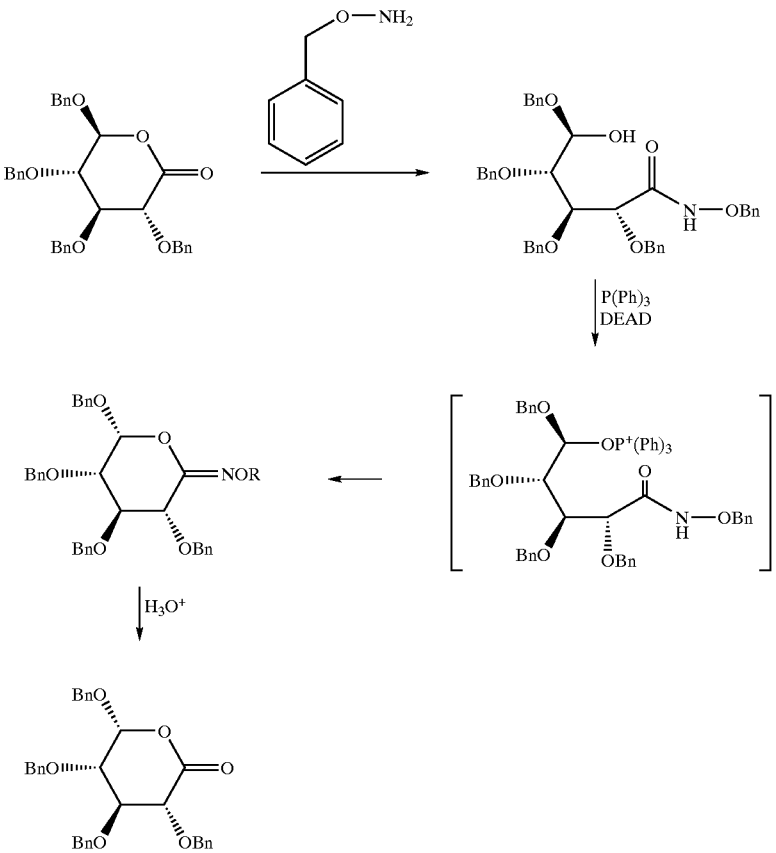

Scheme 5

This method provides a comparatively high reaction yield. However, the starting materials such as benzyloxyamine or DEAD are expensive and thus, uneconomic; the reactant triphenylphosphine is not suitable for being used industrially; and work-up process is not easy due to some side reactions such as the formation of lactam compound by N-cyclization reaction instead of the formation of lactone compound by O-cyclization. Therefore, this method is not appropriate for being utilized in an industrial production.

Therefore, the present inventors have tried to develop a new process effectively converting the chirality of 4- or 5-position carbon in 1,4- or 1,5-lactone compound and as a result thereof, come to the conclusion that such a purpose can be achieved using a secondary amine and a sulfonyl group-containing compound.

The process of Step (a) is preferably carried out in a solvent. Any typical organic solvent which does not adversely affect the reaction may be used, but ethyl acetate, methylene chloride, tetrahydrofuran, pyridine, etc. are preferable. However, alcohol solvents are not appropriate. The reactant secondary amine of formula (4) itself can function as a solvent. Therefore, in such a case, the reaction can proceed smoothly without any need to use a separate solvent. The reactant secondary amine of formula (4) is used in an amount of 1 equivalent or more with respect to the lactone compound of formula (3). Excess amount may be used for providing an additional advantage of the reduction of reaction time with no influence on the yield. As aforementioned, since the secondary amine has the function of solvent or co-solvent in this reaction, it may be used in an excess amount sufficient to dissolve the substances in the reaction system. Among the compounds of formula (4), the preferred ones for being used in the present invention include dimethylamine, diethylamine, diisopropylamine, pyrrolidine and piperidine. The sulfonyl group-containing compound of formula (5) is used in an amount of 1 to 3 equivalents, preferably 2 equivalents with respect to the compound of formula (3). When an amount of more than 3 equivalents is used, it is not easy to remove the unreacted compound of formula (5) during the work up procedure. Among the compounds of formula (5) in the form of halide or anhydride, the preferred one is methane sulfonyl chloride. In the step of reacting the compound of formula (5), one or more selected from a group consisting of pyridine, triethylamine and dimethylaminopyridine can be used as a reaction-aid, and other auxiliaries having the same function as those mentioned above can be used. The reaction is carried out at temperatures around 0° C., preferably at temperatures ranging from −5° C. to 30° C.

In the process of Step (a), the compound of formula (3) is reacted with the secondary amine to form an amide first and then reacted with the sulfonyl group-containing compound of formula (5) to activate the hydroxy group. The activated compound is cyclized again to form a compound having the same structure as the starting compound but the chirality at 4-position carbon of the lactone ring is converted. That is, if the chirality of 4-position carbon of the starting compound is R-configuration, it is converted to S-configuration after the reaction and vice versa. That is, according to the present invention, the product compound does not have a fixed chirality but have a relatively converted chirality at 4-position carbon compared with the starting compound. The total reaction yield of this process is as high as 85% or more.

In Step (b), the compound of formula (6) is reduced by DIBAL-H (diisopropylaluminum hydride) and then reacted with the compound of formula (7) to give the compound of formula (8). The reaction is carried out at temperatures ranging from −78 to −30° C., preferably at −50° C. DIBAL-H and the compound of formula (7) are used in amounts of 1 equivalent and 1 to 2 equivalents (preferably 1.2 equivalent), respectively, with respect to the compound of formula (6). The reaction of DIBAL-H is preferably carried out in a solvent, and as the examples thereof one or more selected from a group consisting of toluene, methylene chloride and tetrahydrofuran can be mentioned. The step of reacting with the compound of formula (7) proceeds in a solvent such as tetrahydrofuran (when R=benzyl, etc.) or pyridine (when R=benzoyl, etc.) and optionally in the presence of a reaction aid such as potassium hydroxide or 18-crown-6.

In Step (c), the compounds of formulae (6) and (8) are oxidized by periodic acid and then reduced by DIBAL-H or NaBH$_4$ to give the compounds of formulae (9) and (10), respectively. The reaction of the compound of formula (6) or (8) with periodic acid results in the quantitative formation of an aldehyde compound. When the aldehyde compound obtained from the compound of formula (6) is reduced by DIBAL-H in an amount of 2.0 equivalents or by NaBH$_4$ in an amount of 0.5 to 1.0 equivalent, preferably 1.0 equivalent with respect to the compound of formula (6), the alcohol compound of formula (9) is given in a yield of 60 to 95%. When the aldehyde compound obtained from the compound of formula (8) is reduced by DIBAL-H or NaBH$_4$ in an amount of 1.0 equivalent with respect to the compound of formula (8), the compound of formula (10) is given in a high yield of 90% or more. The reference (J. Org. Chem., 61, 5178(1996)) may be referred to the specific reaction conditions.

Finally, in Step (d), the compound of formula (9) or (10) obtained in Step (c) is subjected to hydrolysis reaction in a solvent in the presence of an acid or a base to give L-ribose of formula (1). Solvents which can be used include water, dioxane, methanol, ethanol, and mixtures thereof. Reaction temperature and time of Step (d) reaction may be different depending upon the acid or base used. For example, the reaction is carried out for 24 hours at about 40° C. when hydrochloric acid is used, and reflux condition is required when trifluoroacetic acid is used. More specifically, L-ribose of formula (1) can be obtained by hydrolyzing the compound of formula (9) in the presence of an acid, or by hydrolyzing the compound of formula (10) either in the presence of a base and then in the presence of an acid or in the presence of an acid from the first. The specific method to be applied may be selected depending on the kind of substituent R. For example, when the substituent R is benzoyl, it is preferable to select a method wherein hydrolysis reaction is carried out in the presence of a base and an acid by turns. When the substituent R is other than benzoyl, an acid hydrolysis method may be selected. The acid which can be used in Step (d) includes hydrochloric acid, sulfuric acid and trifluoroacetic acid, and the base includes sodium hydroxide and potassium hydroxide. The base or acid is used in a catalytic amount wherein the catalytic amount means about 0.1 equivalent.

L-ribose obtained by the method as explained above may be purified by recrystallization in a solvent or by silica gel column chromatography.

The present invention will be more specifically explained in the following examples. However, it should be understood that the following examples are intended to illustrate the present invention but not in any manner to limit the scope of the present invention.

EXAMPLES

Example 1

Synthesis of 2,3:5,6-di-O-isopropylidene-D-talono-1,4-lactone

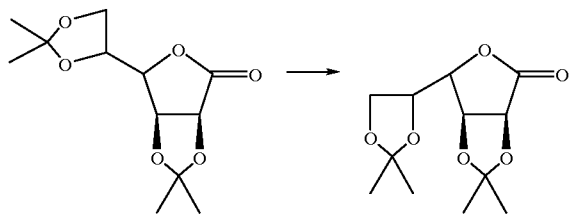

2,3:5,6-Di-O-isopropylidene-D-manono-1,4-lactone (160 g) was dissolved in ethyl acetate (320 ml) and then piperidine (123 ml) was added dropwise thereto at 0° C. After TLC revealed the completion of reaction, excess piperidine and solvent were removed by distillation under reduced pressure. The reactants were dissolved again by adding ethyl acetate (1 l). Subsequently, triethylamine ($Et_3N$; 138 ml) and dimethylaminopyridine (1 g) were added under nitrogen gas stream, and methane sulfonyl chloride (72 ml) was added dropwise at 0° C. After the dropwise addition, the temperature in the reaction vessel was raised to room temperature and the reaction was carried out for about 5 hours. After TLC revealed the completion of reaction, water was added to stop the reaction. The reaction mixture was extracted with ethyl acetate from the aqueous layer, dried over anhydrous magnesium sulfate to remove the moisture in the organic layer, and concentrated under reduced pressure. The residue was purified by silica gel column chromatography (eluent: hexane/ethyl acetate=3/1, v/v) to give the title compound (136 g, Yield 85.0%) as a white solid.

Example 2

Synthesis of 2,3-O-isopropylidene-L-ribofuranose

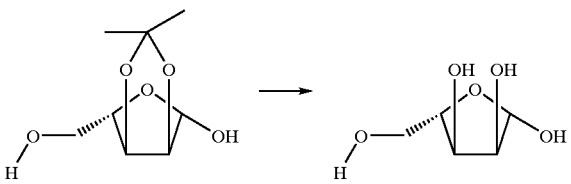

2,3:5,6-Di-O-isopropylidene-D-talono-1,4-lactone (10 g) prepared in Example 1 was dissolved in ethyl acetate (100 ml). Periodic acid (10 g) was added thereto at 0° C. and the resulting mixture was stirred for about 5 hours. After TLC revealed the completion of reaction, the solid in the reaction mixture was removed by filtration and the resulting solution was washed with aqueous sodium chloride solution. The solution was dried over magnesium sulfate to remove the moisture and then distilled under reduced pressure in order to quantitatively give a compound in the form of an oil. The compound thus obtained was dissolved in methylene chloride (100 ml) and 2 equivalents of DIBAL-H was slowly added thereto while maintaining the temperature in the reaction vessel of −50° C. After TLC revealed the completion of reaction, celite (20 g) was added. The reaction mixture was strongly stirred during which 6.0N sodium hydroxide solution (50 ml) was slowly added dropwise. The reaction mixture was filtered to remove the solid therein and then washed with 6.0N sodium hydroxide solution. The organic layer was dried over magnesium sulfate to remove the moisture and distilled under reduced pressure. The residue was purified by silica gel column chromatography (eluent: hexane/ethyl acetate=1/1, v/v) to give the title compound (5.9 g, Yield 80.3%) as an oil.

Example 3

Synthesis of L-ribose

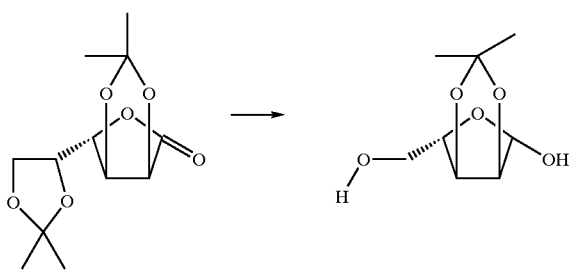

2,3-O-isopropylidene-L-ribofuranose (4.0 g) prepared in Example 2 was dissolved in a solvent mixture of dioxane (8 ml) and water (8 ml), and 1.0N hydrochloric acid solution (200 μl) was added thereto. The reaction proceeded for about 24 hours while maintaining the temperature in the reaction vessel of 40° C. After TLC revealed the completion of reaction, the solvent was removed by distillation under reduced pressure. The residue was dissolved in water (15 ml) which was then washed with ethyl acetate to remove some impurities. Water was removed by distillation under reduced pressure to give a compound in the form of an oil. The compound thus obtained was purified by silica gel column chromatography (eluent: chloroform/methanol=4/1, v/v) to give the title compound (2.2 g, Yield 70%).

Example 4

Synthesis of 1-O-benzoyl-2,3;5,6-di-O-isopropylidene-D-talonofuranoate

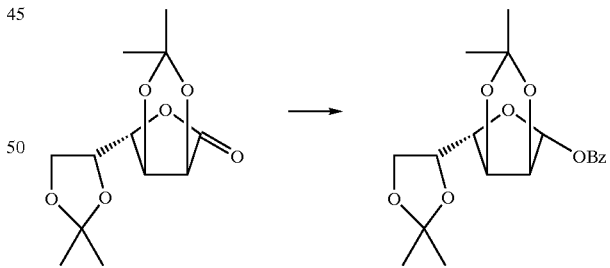

2,3:5,6Di-O-isopropylidene-D-talono-1,4lactone (10 g) prepared in Example 1 was dissolved in toluene (100 ml). 1.0 Equivalent of DIBAL-H was slowly added dropwise under nitrogen atmosphere while maintaining the temperature in the reaction vessel of about −50° C. After TLC revealed the completion of reaction, celite (10 g) was added and then 6.0N sodium hydroxide solution (10 ml) was slowly added dropwise while the reaction mixture was strongly stirred. The reaction mixture was filtered to remove the solid therein and the resulting solution was washed with 6.0N sodium hydroxide solution. The organic layer was dried over magnesium sulfate to remove the moisture and then distilled under reduced pressure to give 2,3:5,6-di-O-isopropylidene-D-talonofuranose (9.4 g) in the form of an oil.

The compound thus obtained (9.4 g) was dissolved in pyridine (20 ml) and the temperature in the reaction vessel was lowered to 0° C. Benzoyl chloride (4.4 ml) was slowly added dropwise thereto and the temperature in the reaction vessel was raised to room temperature. After TLC revealed the completion of reaction, pyridine was removed by distillation under reduced pressure. The residue was dissolved in ethyl acetate (50 ml) and washed with water. The organic layer was dried over magnesium sulfate to remove the moisture and distilled under reduced pressure to give a compound in the form of an oil. The compound thus obtained was purified by silica gel column chromatography (eluent: hexane/ethyl acetate=10/1, v/v) to give the title compound (13 g, Yield 93%) as a white solid.

Example 5

Synthesis of 1-O-benzyl-2,3;5,6-di-O-isopropylidene-D-talonofuranoate

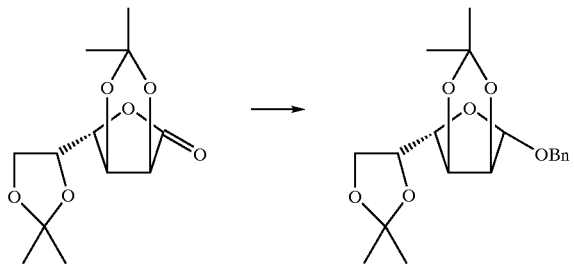

2,3:5,6-Di-O-isopropylidene-D-talono-1,4-lactone (10 g) prepared in Example 1 was dissolved in toluene (100 ml). 1.0 Equivalent of DIBAL-H was slowly added dropwise thereto under nitrogen atmosphere while maintaining the temperature in the reaction vessel of about −50° C. After TLC revealed the completion of reaction, celite (10 g) was added and then 6.0N sodium hydroxide solution (10 ml) was slowly added dropwise during which the reaction mixture was strongly stirred. The reaction mixture was filtered to remove the solid therein and the resulting solution was washed with 6.0N sodium hydroxide solution. The organic layer was dried over magnesium sulfate to remove the moisture and then distilled under reduced pressure to give 2,3:5,6-di-O-isopropylidene-D-talonofuranose (9.4 g) in the form of an oil.

The compound thus obtained (9.4 g) was dissolved in tetrahydrofuran (40 ml), potassium hydroxide (4.5 g) and 18-crown-6 (1.0 g) were added thereto, and the resulting mixture was vigorously stirred. After the temperature in the reaction vessel was lowered to 0° C., benzyl bromide (5 ml) was slowly added dropwise, and the temperature in the reaction vessel was raised to room temperature. After TLC revealed the completion of reaction, the solvent was removed by distillation under reduced pressure. The residue was dissolved in ethyl acetate (100 ml) and washed with water. The organic layer was dried over magnesium sulfate to remove the moisture and distilled under reduced pressure to give a compound in the form of an oil. The compound thus obtained was purified by silica gel column chromatography (eluent: hexane/ethyl acetate=10/1, v/v) to give the title compound (11.9 g, Yield 88%) as a white solid.

Example 6

Synthesis of 1-O-benzoyl-2,3-O-isopropylidene-L-ribonofuranoate

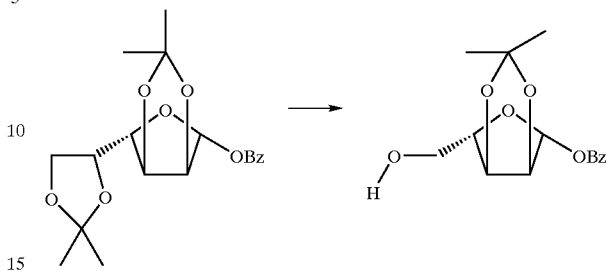

1-O-benzoyl-2,3:5,6-di-O-isopropylidene-D-talonofuranoate (10 g) prepared in Example 4 was dissolved in ethyl acetate (100 ml). Periodic acid (7.6 g) was slowly added thereto at 0° C. and after 5 hours, the completion of reaction was confirmed by TLC. The solid in the reaction mixture was removed by filtration and the resulting solution was washed with aqueous sodium chloride solution. The solution was dried over magnesium sulfate to remove the moisture and then distilled under reduced pressure to give a compound in the form of an oil. The compound thus obtained was dissolved in ethanol (100 ml) and sodium borohydride (NaH$_4$; 1.0 g) was slowly added thereto while maintaining the temperature in the reaction vessel of 0° C. After TLC revealed the completion of reaction, aqueous ammonium chloride solution was added to stop the reaction and the reaction solution was distilled under reduced pressure. The resulting solid was dissolved in ethyl acetate (200 ml) and washed with water. The organic layer was dried over magnesium sulfate to remove the moisture and distilled under reduced pressure to give the title compound (7.4 g, Yield 91%) as a solid.

Example 7

Synthesis of 1-O-benzyl-2,3-O-isopropylidene-L-ribonofuranoate

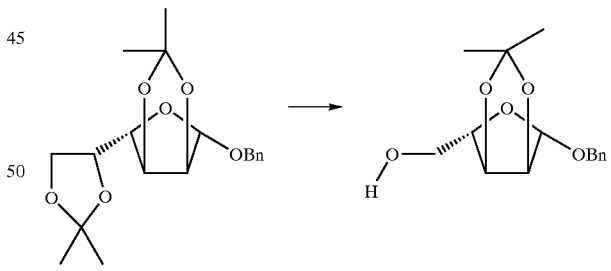

1-O-benzyl-2,3:5,6-di-O-isopropylidene-D-talonofuranoate (10 g) prepared in Example 5 was dissolved in ethyl acetate (100 ml). Periodic acid (7.3 g) was slowly added thereto at 0° C. and after 5 hours, the completion of reaction was confirmed by TLC. The solid in the reaction mixture was removed by filtration and the resulting solution was washed with aqueous sodium chloride solution. The solution was dried over magnesium sulfate to remove the moisture and then distilled under reduced pressure to give a compound in the form of an oil. The compound thus obtained was dissolved in ethanol (100 ml) and sodium borohydride (NaBH$_4$; 0.96 g) was slowly added thereto

Example 8

Synthesis of L-ribose

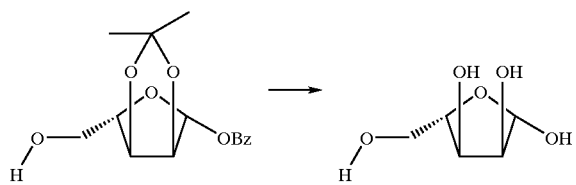

1-O-benzoyl-2,3-O-isopropylidene-L-ribonofuranoate (10 g) prepared in Example 6 was dissolved in a solvent mixture of methanol (30 ml) and 1.0N aqueous sodium-hydroxide solution (10 ml) and then reacted for about 3 hours. After TLC revealed the completion of reaction, the reaction solution was distilled under reduced pressure, water (10 ml) was added, and the reaction mixture was extracted two to three times with ethyl acetate. The extract was dried over magnesium sulfate and distilled under reduced pressure to give 2,3-isopropylidene-L-ribose (6.0 g). The compound thus obtained was dissolved in a solvent mixture of dioxane (12 ml) and water (12 ml), 1.0N hydrochloric acid solution (200 µl) was added, and then reaction was carried out for about 24 hours while maintaining the temperature of the reaction vessel of 40° C. After TLC revealed the completion of reaction, the solvent was removed by distillation under reduced pressure. The residue was dissolved in water (30 ml) and washed with ethyl acetate. Water was removed by distillation under reduced pressure to give a compound in the form of an oil. The compound thus obtained was purified by silica gel column chromatography (eluent: chloroform/methanol=4/1, v/v) to give the title compound (4.1 g, Yield 80%).

Example 9

Synthesis of L-ribose

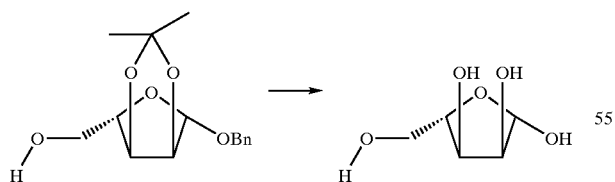

1-O-benzyl-2,3-O-isopropylidene-L-ribonofuranoate (10 g) prepared in Example 7 was dissolved in 3% TFA solution (30 ml) and reacted under reflux for 3 hours. After TLC revealed the completion of reaction, the solvent was removed by distillation under reduced pressure. The residue was purified by silica gel column chromatography (eluent: chloroform/methanol=4/1, v/v) to give the title compound (4.5 g, Yield 84%).

INDUSTRIAL APPLICABILITY

According to the process as explained above, L-ribose which is a key intermediate for preparing the L-nucleoside based medicines can be effectively prepared.

What is claimed is:

1. A process for preparing L-ribose of the following formula (1):

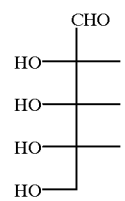
(1)

characterized in that (a) a compound of the following formula (3):

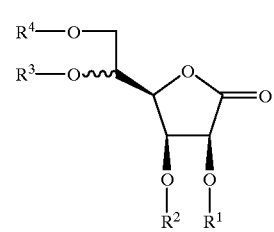
(3)

wherein $R^1$, $R^2$, $R^3$ and $R^4$ independently of one another represent $C_2$–$C_6$-carbonyl, benzoyl or benzyl, or $R^1$ and $R^2$, or $R^3$ and $R^4$ may combine with each other to form isopropylidene or cyclohexylidene, is reacted with a secondary amine of the following formula (4):

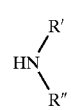
(4)

wherein R' and R" are identical with or different from each other and independently of one another represent straight-chain or branched $C_1$–$C_6$-alkyl, or may combine together with the nitrogen atom to which they are attached to form 4- to 7-membered saturated heterocycle, and then reacted with a sulfonyl group-containing compound of the following formula (5):

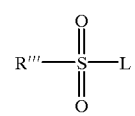
(5)

wherein R''' represents straight-chain or branched $C_1$–$C_6$-alkyl, phenyl or tolyl, and L represents reactive leaving group, preferably halogen or

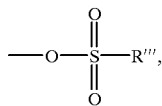

to give a compound of the following formula (6):

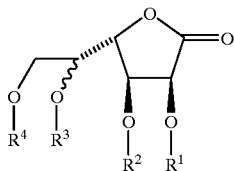
(6)

wherein $R^1$, $R^2$, $R^3$ and $R^4$ are defined as above, which has a converted chirality at 4-position carbon as compared with the compound of formula (3);

(b) the compound of formula (6) is reduced by DIBAL-H and then reacted with a compound of the following formula (7):

RX    (7)

wherein R represents benzyl, benzoyl, $C_1$–$C_4$-alkanoyl or $C_1$–$C_4$-alkyl, and X represents halogen, to give a compound of the following formula (8):

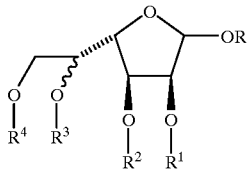
(8)

wherein $R^1$, $R^2$, $R^3$, $R^4$ and R are defined as above;

(c) the compounds of formulae (6) and (8) are reacted with periodic acid and then reduced by DIBAL-H or $NaBH_4$ to give compounds of the following formulae (9) and (10), respectively:

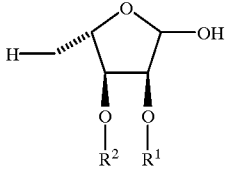
(9)

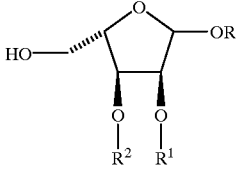
(10)

wherein $R^1$, $R^2$ and R are defined as above; and (d) the compound of formula (9) or (10) thus obtained is subjected to a hydrolysis reaction in a solvent.

2. The process of claim 1 wherein the secondary amine of formula (4) in Step (a) is one or more selected from a group consisting of dimethylamine, diethylamine, diisopropylamine, pyrrolidine and piperidine.

3. The process of claim 1 wherein the sulfonyl group-containing compound of formula (5) in Step (a) is methane sulfonyl chloride.

4. The process of claim 1 wherein triethylamine and dimethylaminopyridine are used as a reaction aid together with methane sulfonyl chloride.

5. The process of claim 1 wherein DIBAL-H and the compound of formula (7) are used in an amount of 1 equivalent and 1 to 2 equivalents, respectively, with respect to the compound of formula (6) in Step (b).

6. The process of claim 1 wherein the step of reacting with the compound of formula (7) is carried out optionally in the presence of one or more reaction aids selected from a group consisting of potassium hydroxide and 18-crown-6.

7. The process of claim 3 wherein triethylamine and dimethylaminopyridine are used as a reaction aid together with methane sulfonyl chloride.

8. The process of claim 5 wherein the step of reacting with the compound of formula (7) is carried out optionally in the presence of one or more reaction aids selected from a group consisting of potassium hydroxide and 18-crown-6.

* * * * *